United States Patent [19]

Kludas

[11] Patent Number: 5,055,298
[45] Date of Patent: Oct. 8, 1991

[54] COSMETIC COMPOSITION COMPRISING AN EXTRACELLULAR CONNECTIVE TISSUE MATRIX

[75] Inventor: Martin Kludas, West Berlin, Fed. Rep. of Germany

[73] Assignee: Chemisches Laboratorium Dr. Kurt Richter GmbH, Berlin, Fed. Rep. of Germany

[21] Appl. No.: 917,468

[22] Filed: Oct. 10, 1986

[51] Int. Cl.$^5$ .................... A61K 7/00; A61K 37/00
[52] U.S. Cl. ........................................ 424/401; 514/8; 514/21; 514/846
[58] Field of Search ................. 514/21, 9, 773, 844, 514/845, 8, 846, 847, 848, 938; 530/356, 851, 849, 829, 395; 424/401

[56] References Cited

U.S. PATENT DOCUMENTS

| Re. 30,239 | 3/1980 | Kuettner et al. ................. 424/95 |
| 3,839,590 | 10/1974 | Battista ........................ 514/844 X |
| 3,887,703 | 6/1975 | Manoussos et al. .............. 424/95 |
| 3,991,184 | 11/1976 | Kludas et al. ................... 514/21 |
| 4,042,457 | 8/1977 | Kuettner et al. . |
| 4,108,849 | 8/1978 | Thomas .......................... 260/122 |
| 4,141,973 | 2/1979 | Balazs . |
| 4,228,153 | 10/1980 | Burov et al. .................... 424/95 |
| 4,296,099 | 10/1981 | Berrebi et al. .................. 424/105 |
| 4,327,078 | 4/1982 | Charlet et al. .................. 424/45 |
| 4,389,487 | 6/1983 | Ries ............................ 435/273 |
| 4,420,339 | 12/1983 | Kato ............................ 106/124 |
| 4,448,718 | 5/1984 | Yannas et al. .................. 260/123.7 |
| 4,451,397 | 5/1984 | Huc et al. ...................... 530/356 |
| 4,464,362 | 8/1984 | Kludas et al. ................... 424/95 X |
| 4,488,911 | 12/1984 | Luck et al. ..................... 106/161 |
| 4,511,653 | 4/1985 | Play et al. ..................... 435/69 |
| 4,642,292 | 2/1987 | Reid et al. ..................... 435/267 |
| 4,664,110 | 5/1987 | Schanzlin ...................... 128/303.1 |
| 4,696,813 | 9/1987 | Higa ............................ 514/21 X |
| 4,736,024 | 4/1988 | Della Valle et al. . |

FOREIGN PATENT DOCUMENTS

| 0128706 | 12/1984 | European Pat. Off. . |
| 0154447 | 9/1985 | European Pat. Off. . |
| 1730 | 3/1963 | France . |
| 6652 | 3/1969 | France . |
| 2299019 | 8/1976 | France . |
| 7503504 | 8/1976 | France . |
| 2487197 | 1/1982 | France . |
| 7912040 | 1/1982 | France . |
| 2591107 | 6/1987 | France . |
| 1386864 | 3/1975 | United Kingdom . |

OTHER PUBLICATIONS

S. A. Barkhas, Placenta as a Plastic Material in Opthalmosurgery, Opthamology Reports, vol. XVII, 758–761 (1940).

Primary Examiner—John S. Maples
Attorney, Agent, or Firm—Pennie & Edmonds

[57] ABSTRACT

A cosmetic agent for remodeling and repairing the basement membrane of aging human skin and/or human skin damaged, for example, by ultraviolet radiation. The agent contains the essential components of the extracellular connective tissue matrix in native form and in physiological proportions. The components are obtained from mammals.

18 Claims, No Drawings

COSMETIC COMPOSITION COMPRISING AN EXTRACELLULAR CONNECTIVE TISSUE MATRIX

INTRODUCTION

This invention relates to cosmetic agents and compositions for the repair and remodeling of damaged basement membranes of the human skin. This invention also relates to a method for treating damaged human skin with these agents and compositions.

Basement membrane damage and damage to the epidermal and dermal layers of the skin have been attributed to a variety of factors. Some of these factors are ultraviolet radiation and aging. Aging skin and/or skin damaged by ultraviolet radiation has characteristic ruptures and discontinuities in the basement membrane. It is important from a cosmetic point of view to conserve an intact basement membrane and to repair or remodel damaged basement membranes in human skin. A damaged basement membrane results in limited functionality and aberrations in the physiological dermal-epidermal interactions.

The underlying problem addressed by the present invention has been the inability, to date, to provide a composition or treatment which would enable the conservation and/or repair and remodeling of a basement membrane damaged by factors such as aging or exposure to environmental factors such as ultraviolet light. This invention, therefore, relates to cosmetic agents, compositions and methods for their use which, utilizing appropriate therapy, maintain an intact basement membrane and are effective in repairing and remodeling damaged basement membranes. More specifically, the cosmetic agents utilized in this invention provide essential components of the extracellular connective tissue matrix in their natural or native, unaltered structural form, which repair damaged basement membranes of skin. The result of treatment with these cosmetic agents is an enhanced and healthy skin wherein the normal physiological functioning and interactions between the various layers of the skin have been restored.

BACKGROUND OF THE INVENTION
SKIN STRUCTURE

Generally stated, the skin consists of two layers that are completely different in character. The more superficial and thinner layer, the epidermis, is epithelial tissue that is derived from ectoderm. The deeper and thicker layer, the dermis, consists of connective tissue that is derived from mesoderm. These two layers are firmly cemented together to form a cohesive membrane—the skin—which varies in thickness from less than 0.5 mm. to 3 or even 4 mm. or more in different parts of the body. The skin rests on subcutaneous tissue which is sometimes called the hypodermis, but is not, like the epidermis, considered part of the skin. Irregularly spaced bundles of collagenic fibers extend from the dermis into the subcutaneous tissue to provide anchorage for the skin. The subcutaneous tissue permits the skin over most parts of the body to have considerable latitude of movement.

The epidermis of the skin is composed of stratified squamous keratinizing epithelium. Like all epithelium, the epidermis contains no capillaries, so that it is nourished by diffusion from capillaries that are in the deeper layer of the skin, the dermis.

Since keratin is continuously worn away or shed from the surface, it must be continuously added to from beneath by the changing of living cells into keratin. this requires that the living cells of the epidermis continuously proliferate to maintain their numbers.

Many processes are in more or less continual operation in the epidermis: (1) cell division in the deep layers, (2) cells being pushed toward the surface as a result, (3) cells farthest from the dermis being transformed into keratin and (4) keratin desquamating from the surface. If these 4 processes are not synchronized properly—and in many skin conditions caused by age, exposure to ultraviolet radiation or disease, they are not—the character of the epidermis changes greatly.

The innermost of the inner layers is composed of basal cells that sit on the basal lamina that separates the epidermis from the underlying dermis. All epithelial tissues have on their basal surface this continuous sheet-like extracellular structure in contact with the underlying connective tissue. In some epithelial tissues (e.g., the skin) subject to friction, the basal lamina is anchored to the subjacent connective tissue by small fibers of collagen called anchoring fibers.

In most epithelia, fibrils of collagen (reticular fibers) complexed with amorphous protein-polysaccharides constitute another layer beneath the basal lamina called the fibrous or reticular lamina. This is a considerably thicker structure. Three constituents—basal lamina, ground substance (a highly hydrated, gel-like substance comprised of glycosaminoglycan and proteoglycan molecules), and reticular fibers—form what is called the basement membrane. The collagen of the basal lamina is primarily of type IV and that of the subjacent reticular fibers is probably type III collagen. The thick fibers below this layer are known to be formed by collagen type I. In this specification the term basement membrane will be reserved for the thicker structures visible with the light microscope. In current usage, the terms basal lamina and basement membrane are frequently used interchangeably.

Basal laminae, therefore, are thin layers of specialized extracellular matrix that underlie all epithelial cell sheets (and tubes). They also surround individual muscle cells, fat cells, and Schwann cells (which wrap around peripheral nerve fibers to form myelin). The basal lamina, thus, separates these cells and cell sheets from the underlying or surrounding connective tissue. However, there is increasing evidence that basal laminae serve more than simple structural and filtering roles. They seem to be able to induce cell differentiation, influence cell metabolism, organize the proteins in adjacent plasma membranes, and serve as specific "highways" for cell migration.

The basal lamina is synthesized by the cells that rest on it. Although the precise composition varies from tissue to tissue, and even from region to region within the same lamina, a major component of all basal laminae as noted above is type IV collagen. Type IV proalpha-chains are unusual in having extra-long extension peptides that are probably not cleaved after secretion. These procollagen molecules do not form typical collagen fibrils, although they do become covalently cross-linked to each other. In addition to proteoglycans and fibronectin, which are important constituents of basal laminae, the large glycoprotein laminin has been shown to be a major component of all basal laminae studied so far. It consists of at least two subunits (220,000 and 440,000 daltons) that are disulfide-bonded to each other.

Basal laminae undoubtedly contain may other proteins yet to be identified. The detailed molecular organization of basal laminae is unknown, although there is some evidence that laminin and proteoglycan molecules are concentrated along the inner and outer surfaces of the basal lamina, with collagen molecules sandwiched in the middle. See also, Briggaman, Biochemical Composition of the Epidermal Dermal Junction and other Basement Membranes, *Invest.Dermatology*, 78(1): 1-6 (1982).

Basal laminae have been shown to perform a surprising diversity of functions. The basal lamina may act as a selective cellular barrier: for example, the lamina beneath epithelial cells prevents fibroblasts in the underlying connective tissue from making contact with the epithelial cells, but it does not stop macrophages, lymphocytes, or nerve processes from passing through it. It is likely that the basal lamina plays an important part in tissue regeneration after injury. When tissues such as muscle, nerve, and epithelia are damaged, the basal lamina survives and provides a scaffolding along which regenerating cells can migrate. In this way, the original tissue architecture is readily reconstructed.

However, recent research on connective tissue has led to the conclusion that with the aging of the skin fundamental structural modifications occur, especially in the basement membrane. These problems are of special significance to skin-care cosmetics. Since the extracellular connective tissue matrix produces an environment in which cells perform their function, the physiological interaction between cells and extracellular matrix is one of the key elements for normal epidermal-dermal interactions via an intact basement membrane.

Beyth and Culp (Mech. Aging Devel. 29: 151, 1985) point out that the significant physical and chemical modifications observed in the aging process are a consequence of a modified extracellular matrix. Pieraggi et al. (Virch. Arch. 1985) found a shift of the physiological equilibrium between skin fibroblasts and the extracellular matrix in aging skin. Sengel (Development Mechanisms, A. R. Liss, New York, pp. 123-135, 1985) points out the significance of the extracellular matrix, including the intact basement membrane, for the transmission of morphogenetic signals. The disturbance of the normal interactions between the epidermis and the dermis in aged skin is also known from ultrastructural investigations of the basement membrane. In addition, sunlight (ultraviolet) is known to injure the skin, not only by causing sunburn in the epidermis and inducing pigmentation, but by inducing changes in the basal membranes and deeper layers (dermis) below the epidermis. These changes appear later as premature aging of the skin —wrinkling, mottling, change in suppleness of the skin (altered connective tissue), dryness and alterations in the blood vessels. Ultraviolet radiation may also be absorbed by and damage DNA in cells present in the skin. It is further implicated in causing skin cancer.

Therefore, one may conclude that damage or injury to the basal laminae would have serious consequences for the entire epidermal layer and could very well result in associated detrimental cosmetic implications.

EXTRACELLULAR MATRIX

Most cells in multicellular organisms are in contact with an intricate meshwork of interacting, extracellular macromolecules that constitute the extracellular matrix. These versatile protein and polysaccharide molecules are secreted locally and assemble into an organized meshwork in the extracellular space of most tissues. In addition to serving as a type of universal biological glue, they also form highly specialized structures such as cartilage, tendons, basal laminae, and (with the secondary deposition of a form of calcium phosphate crystals) bone and teeth.

Until recently, the vertebrate extracellular matrix was thought to serve mainly as a relatively inert scaffolding that stabilized the physical structure of tissues. But now it is clear that the matrix plays a far more active and complex role in regulating the behavior of the cells that contact it—influencing their development, migration, proliferation, shape, and metabolic functions.

The macromolecules that constitute the extracellular matrix are secreted by local cells, especially fibroblasts, which are widely distributed in the matrix. Two of the main classes of extracellular macromolecules that make up the matrix are (1) the collagens and (2) the polysaccharide glycosaminoglycans, which are usually covalently linked to protein to form proteoglycans. The glycosaminoglycan and proteoglycan molecules form a highly hydrated, gel-like "ground substance" in which collagen fibers are embedded. While the long collagen fibers strengthen and help to organize the matrix, the aqueous phase of the polysaccharide gel permits the diffusion of nutrients, metabolites, and hormones between the blood and the tissue cells. In many cases, fibers of the rubberlike protein elastin are also present and impart resilience to the matrix. In addition, two high molecular weight glycoproteins are among the major components of extracellular matrices: fibronectin, which is widely distributed in connective tissues, and laminin, which has so far been found only in basal laminae.

The term connective tissue is often used to describe the extracellular matrix plus the cells found in it, such as fibroblasts, macrophages, and mast cells. The amount of connective tissue in organs varies greatly: skin and bone are composed mainly of connective tissue, whereas the brain and spinal cord contain very little. Moreover, the relative amounts of the different types of matrix macromolecules and the way that they are organized within the extracellular matrix vary enormously, giving rise to a diversity of forms, each highly adapted to the functional requirements of the particular tissue. Thus, the matrix can become calcified to form the rock-hard structures of bone or teeth, or it may take on the ropelike organization of the collagen fibers in tendons, which gives them their enormous tensile strength.

The collagens are a family of highly characteristic fibrous-proteins found in all multicellular animals. They are the most abundant proteins in mammals, constituting 25% of their total protein. The central feature of all collagen molecules is their stiff, triple-stranded helical structure. Three collagen polypeptide chains, called alpha-chains, are wound around each other in a regular helix to generate a ropelike collagen molecule about 300 nm long and 1.5 nm in diameter. Seven genetically distinct collagen alpha-chains, each about 1000 amino acid residues long, have been well defined.

The major types are referred to as types I, II, III, IV and V. Types I, II and III are the main types of collagen found in connective tissues, and of these, type I is much the most common, constituting 90% of the collagen in the body. After being secreted into the extracellular space, types I, II and III collagen molecules assemble into ordered polymers called collagen fibrils, which are long (up to many microns), thin (10 to 300 nm in diameter), cablelike structures clearly visible in electron micrographs. Such fibrils are often grouped into larger bundles, which can be seen in the light microscope as collagen fibers several microns in diameter. Type IV molecules (the main collagen in basal laminae) and type V (found in small amounts in basal laminae and elsewhere) do not form fibrils.

Tissue such as skin requires elasticity in addition to tensile strength in order to function. An extensive network of elastic fibers in the extracellular matrix of these tissues gives them the required ability to recoil after transient stretch. The main component of elastic fibers is elastin, a 70,000-dalton glycoprotein, which, like collagen, is unusually rich in proline and glycine but, unlike collagen, contains little hydroxyproline and no hydroxylysine.

Glycosaminoglycans, formerly known as mucopolysaccharides, are long, unbranched polysaccharide chains composed of repeating disaccharide units. They are now called glycosaminoglycans because one of the two sugar residues in the repeating disaccharide is always an amino sugar (N-acetylglucosamine or N-acetylgalactosamine). Glycosaminoglycans are highly negatively charged due to the presence of sulfate or carboxyl groups or both on many of the sugar residues. Seven groups of glycosaminoglycans have been distinguished by their sugar residues, the type of linkage between these residues, and the number and location of sulfate groups. They are hyaluronic acid (the only group in which none of the sugars is sulfated), chondroitin 4-sulfate, chondroitin 6-sulfate, dermatan sulfate, heparan sulfate, heparin, and keratan sulfate.

Hyaluronic acid (also called hyaluronate) exists as a single, very long carbohydrate chain of several thousand sugar residues in a regular, repeating sequence of disaccharide units. Hyaluronic acid, however, is not typical of the glycosaminoglycans. First, the others tend to contain a number of different disaccharide units arranged in more complex sequences. Second, the others have very much shorter chains, consisting of fewer than 300 sugar residues. Third, all of the other glycosaminoglycans are covalently linked to protein to form proteoglycan molecules (formerly called mucoproteins).

Proteoglycans are different from typical glycoproteins. Glycoproteins usually contain from 1% to 60% carbohydrate by weight in the form of numerous, relatively short (generally less than 15 sugar residues), branched oligosaccharide chains of variable composition, which often terminate with sialic acid. In contrast, proteoglycans are much larger (up to millions of daltons), and they usually contain 90% to 95% carbohydrate by weight in the form of many long, unbranched glycosaminoglycan chains, usually without sialic acid.

Non-collagen glycoproteins that are present in the extracellular matrix include fibronectin, a fiber-forming glycoprotein (about 5% carbohydrate by weight) composed of two disulfide-bonded subunits of 220,000 daltons each. Fibronectin exists as large aggregates in the extracellular space. While most of the protein is not directly bound to cells, some of it is bound to the surfaces of fibroblasts and other cells when they are grown in culture. Purified fibronectin has been shown to promote the adhesion of a variety of cell types to other cells, as well as to collagen and other substrates.

In sum, all cells in tissues are in contact with an intricate extracellular matrix. This matrix not only holds the cells together in tissues, and tissues together in organs, but it also influences the development, polarity, and behavior of the cells it contacts. The matrix contains three major fiber-forming proteins—collagen, elastin, and fibronectin—which are interwoven in a hydrated gel formed by a network of glycosaminoglycan chains. All of the macromolecules are secreted locally by cells in contact with the matrix.

The collagens are ropelike, triple-stranded, helical molecules that aggregate in long cablelike fibrils or sheets in the extracellular space. These fibrils in turn can assemble in a variety of highly ordered arrays. Elastin molecules form an extensive cross-linked network of fibers and sheets that can stretch and recoil, imparting elasticity to the matrix. Fibronectin molecules form fibers that promote cell adhesion. The glycosaminoglycans are a heterogeneous group of long, negatively charged polysaccharide chains that (except for hyaluronic acid) are covalently linked to protein to form giant proteoglycan molecules. All of these matrix proteins and polysaccharides are thought to interact and to assemble in a large variety of different three-dimensional structures, ordered in part by the cells secreting the matrix. Since the orientation of the matrix will in turn influence the orientation of the cells it contains, order is likely to be propagated from cell to cell through the matrix.

Research in the fields of cell biology and embryology has also shown that an extracellular connective tissue matrix consisting of genetically distinct collagen types, proteoglycans and structural glycoproteins has a significant influence on cell proliferation, mitogenesis and morphogenesis (Hay, *Mod. Cell. Biol.*, 2: 509, 1983; Bernfield et al. in: The Role of Extracellular Matrix in Development, A. R. Liss, New York, 1984). It has been postulated that there exists a "dynamic reciprocity" between the extracellular matrix on the one hand, and the cytoskeleton and the nuclear matrix on the other hand. The extracellular matrix is thought to exert physical and chemical influences on the geometry and the biochemistry of the cell via transmembrane receptors so as to alter the pattern of gene expression by changing the association of the cytoskeleton with the mRNA, and the interaction of the chromatin with the nuclear matrix. Bissell, et al., *J. Theor. Biol.*, 99: 31-68 (1982).

The following references provide additional information concerning the extracellular matrix and its interactions with other tissue or cellular components. See, Hay, Cell, Cell and Extracellular Matrix, *Modern Cell Biology*, 2: 509-548 (1983) and Kleinman, et al, Role of Collagenous Matrices in the Adhesion and Growth of Cells, Cell Bio., 88 (3): 473-486 (1981).

These factors, when combined with the knowledge that these matrix macromolecules are further known to individually to affect the behavior of cells in culture, has lead the art to attempt to provide them topically to a live but damaged or aging skin surface in order to obtain beneficial effects.

COSMETIC SKIN TREATMENT

In cosmetic skin preparations, individual active substances or combinations of isolated individual components of the extracellular matrix are often used in the hope of preventing skin aging by substitution of deficient or damaged skin components.

For instance, skin preparations are disclosed in the German Patent DE-PS 20 64 604. This reference speaks of increasing the soluble, i.e. not cross-linked portion of the collagen in the skin, by using native soluble collagen (tropocollagen) to improve the age-dependent ratio of soluble to insoluble collagen in favor of the soluble fraction, and to slow down the loss of elasticity of the skin.

A cosmetic preparation containing collagen of the basement membrane is also disclosed in German Patent DE-PS 30 46 133. In contrast to the use of the interstitial collagen types I, II and III which are structurally similar to each other, the use of the basement membrane collagen (collagen type IV) is therein claimed to have a higher effectiveness, since said basement membrane collagen is adopted better by the cells. The stated object of using basement membrane collagen was to promote regeneration and faster growth of new skin cells. Thus the cosmetic preparation tries to counteract a feature of skin aging by supplying an individual substance.

U.S. Pat. No. 4,451,397 discloses the use of collagen in connection with mucopolysaccharides for cosmetic purposes. The main subject matter of the invention disclosed in this patent is a method for producing a solution or a homogeneous gel composition consisting of the aforementioned substances, and the use of these substances in a cosmetic preparation to improve skin tone. Chemical Abstracts, Vol. 101, 1984, No. 78679 b discloses a cosmetic preparation containing fibronectin, which serves as a nutrient for the skin.

Other references additionally disclose the use of connective tissue components for skin treatment. U.S. Pat. No. 3,991,184 to Kludas discloses the use of untreated, soluble collagen having an unchanged substantially non-cross-linked structure for use in treating the skin. U.S. Pat. No. 4,327,078 to Charlet et al. discloses cosmetic agents containing, as an active ingredient, soluble elastin for treatment of aging skin. In addition, U.S. Pat. No. 4,464,362 discloses cosmetic compositions containing inactive cultures of bacteria of the genus Bifidobacterium or bacteria related to this genus for promoting DNA repair in skin cells.

The hitherto known cosmetic agents and the active substances and combinations of different individual substances which have been used, have so far not considered the latest findings of research in connective tissue and cell biology. Significant modifications in epidermal-dermal interactions and in the basement membrane involved in the aging of the skin as well as in the damage caused by ultraviolet light exposure have not yet, until this invention has been completely resolved by the art.

Therefore, it is an object of the present invention to counteract inadequate cell-matrix interaction, due to aging and ultraviolet light exposure, to repair or remodel the basement membrane which is characterized by rupturing and discontinuity in aging skin, and to enable normal interactions of epidermis and dermis to occur via a reconstituted, repaired, and remodeled basement membrane.

SUMMARY OF THE INVENTION

Prior to the present invention, the art had not provided a composition or means for treating aging or damaged skin which resulted in repair or remodeling of the basement membrane. One possible reason for this was the absence in the art of a composition or agent which included all of the essential components of the extracellular connective tissue matrix which is required for growth and health by the basement membrane. In addition, the individual components or mixtures of extracellular connective tissue which were provided by the art were often modified in terms of their structure or were not provided in the same physiological proportions in which they existed in vivo.

The present invention provides a novel cosmetic agent comprised of an extracellular connective tissue matrix wherein all of the extracted components are in the same structural form in which they existed in vivo and are in the same physiological proportions to each other in which they existed in vivo. It is also an aspect of this invention that this cosmetic agent be combined with an acceptable cosmetic carrier to form a cosmetic composition. This invention also provides for the utilization of the cosmetic agent or cosmetic composition in a method for treatment of aged or damaged skin, so as to result in a repair or remodeling of the basement membrane. It is a goal of this treatment that the skin will visually improve in appearance as a result of repair or remodeling of the basement membrane. The precise details of the invention will be further described below.

DESCRIPTION OF THE INVENTION

SOURCE, COMPOSITION AND EXTRACT PREPARATION

According to the present invention, damaged or aged skin is provided with the essential components as extracts of the extracellular connective tissue matrix in their native in vivo structural form as a novel cosmetic agent. These components are provided in their naturally occurring physiological proportions as represented in their particular extracellular connective tissue matrix source.

Surprisingly, it has been discovered that topical application of the essential components of an extract of the extracellular connective tissue matrix in physiological proportions leads to a remodeling or repair of the basement membrane damaged by aging or environmental factors such as ultraviolet light. Normal dermo-epidermal interactions are restored with the remodeling or repair of the basement membrane. This invention enables aging or damaged skin to conserve an adequate extracellular environment which is desirable cosmetically.

The structure and composition of the essential components of the extracellular connective tissue matrix in physiological proportions and in their native structural form in vivo according to the present invention can be illustrated by one process set forth below for their preparation. This procedure is merely an exemplary way to extract the essential components of the extracellular connective tissue matrix in their native structural forms and in the same proportion as their proportions in vivo. The reference, Miller, E. J. et al., preparation and characterization of the different types of collagen, *Methods in Enzymology*, 82 Part A: 33–64 (1982) also discloses extraction methods useful in preparation of the extract of this invention.

Fetal or fetal associated membranes of mammals which are preferably used as starting material can be, for example, placenta, blood vessels and umbilical cords as a sole source or in admixture with each other. The mammalian membrane source may be mammals such as cows (bovine), sheep (ovine), or pigs (porcine).

First, the membranous tissue is rinsed with water to remove the blood. The tissue is then defatted, preferably with acetone, frozen preferably in liquid nitrogen and minced in a mill, e.g. in a blender. The disintegrated tissue obtained in this way is pre-treated with known protease inhibitors (as cited in Miller, supra) in appropriate buffer solutions of relatively high ionic strength (such as 1M NaCl). The purpose of said treatment is to minimize proteolysis by endogenous proteases, by inactivating the proteases. After an incubation, preferably for about one hour, the disintegrated tissue is separated, preferably centrifuged, and the sediment is thoroughly washed with water, preferably at ambient temperature.

The tissue mass treated in this way is solubilized by adjusted and graduated steps of extraction to obtain native components in the same physiological proportions as in the original membrane source.

In the first extraction step, the native, acid-soluble collagen molecules of types I and III are extracted preferably at about 4° C. under acidic condition (preferably of less than pH5) and low ionic strength according to methods known in the art. (Piez et al., Biochemistry 2, 58 (1963); Orekhovitch et al., Biockhimya 13, 55 (1948); Kulonen et al., Proc. Soc. Exp. Biol. Med. 84, 424 (1954); Gallop, Arch. Bioch. Bioph. 54, 486 (1966)). Acetic acid, preferably of a concentration of about 0.1 to 0.5M, is preferably used as extracting agent. However, formic acid of the same concentration, or acidic phosphate or citrate buffer, preferably at a concentration of 0.15 to 1.0M, may also be used.

The suspension containing the collagen is separated preferably by centrifugation and the sediment is washed in de-ionized water preferably about five times.

The washed sediment is then subsequently extracted to obtain proteoglycans and glycoproteins, such as fibronectin and laminin, and other known extracellular matrix components according to methods known in the art (cf. Sajedera et al., J. Biol. Chem. 244, 77 (1969)) preferably using salt solutions of high ionic strength, such as 1M NaCl. However, other salt solutions, such as 2M $MgCl_2$, 2M to 4M guanidine hydrochloride or 5M urea, may also be used.

The suspension obtained in this step is separated preferably by centrifugation. The supernatant, which is retained, contains the desired solubilized components in their native form. The sediment is again thoroughly washed in de-ionized water preferably about five times.

In a third extraction step, collagen of types IV, V, VI and VII, and collagens of types I and III which are more cross-linked and which could not be extracted in the first extraction step by the method described herein, are solubilized by a limited proteolysis, preferably using pepsin, preferably at temperatures from about 4 to about 18° C. (Miller et al., Biochemistry 11, 4903, 1972). The extract is separated preferably by centrifugation.

Preferably the proteolytic extraction step is repeated in order to obtain an extraction which results in a complete solubilization of the starting material.

Each individual extract obtained by the three extraction steps described above is adjusted to a pH-value of preferably 4.5 to 5.0. The extracts are then mixed by constant stirring at a low temperature, preferably about 4° C., until a homogeneous phase is obtained.

The mixture obtained in this way is the inventive cosmetic agent of the extracellular connective tissue matrix extract in physiological proportions and in their native form. These solubilized components are present in macromolecular aggregates.

TREATMENT OF SKIN CONDITIONS

The cosmetic agent, as disclosed below, may be mixed with an acceptable cosmetic carrier to form a cosmetic composition which may be directly or topically applied to human skin. This cosmetic composition or cosmetic agent may be applied to the skin in biologically or therapeutically effective amounts over a period of time which is sufficient to result in repair or remodeling of the basal lamina or basement membrane This repair or remodeling will typically be apparent from a visible improvement of the appearance of the outside of the skin. While not intending to be bound by any theory or mechanism, it is believed that since there is such a strong and irrefutable interrelationship between the basement membrane and the other layers of the skin in the dermis and epidermis, a positive repairing and remodeling effect in the basement membrane will lead to a reestablishment of normal and healthy interactions with and between these other skin layers. It is this reestablishment in part, which is contributing to the overall improvement in the health and appearance of the skin.

The particular amount of cosmetic agent or composition to be applied to the skin and the duration or number of applications can be determined easily on an individual basis by utilizing the agent or composition until a visible improvement of the outer surface of the skin results. One skilled in the art of dermatological medicine or cosmetology and who is familiar with standard topical treatment means would also be in a position to easily evaluate a beneficial course of treatment. Examples of typical and preferable treatments would be application two or three times a day with a cosmetic composition containing about 10% of the cosmetic agent. The percentage of cosmetic agent present in the composition would vary, of course, depending upon the cosmetic carrier and the severity of the skin condition to be treated by the agent. In the most severe cases, the cosmetic agent exclusively may be utilized directly or topically without any other cosmetic carrier.

The effectiveness of a cosmetic agent according to the present invention was demonstrated in the Examples which follow.

EXAMPLES

EXAMPLE 1—CLINICAL TESTS AND RESULTS

Marked areas of the dorsal (back of hand) skin of volunteers having clinical signs of aging skin were treated with the following test creams for four weeks, twice a day:
a) cream (oil-in-water) having 10% of the active composition (extracellular connective tissue matrix extract prepared according to the present invention);
b) cream base (oil-in-water) as control.

Punch biopsies of the treated skin areas were taken and frozen sections were prepared. Using a monoclonal antibody against basement membrane collagen of type IV, immunofluorescence tests were carried out in order to visualize the dermo-epidermal basement membrane.

The skin areas treated with the control cream showed a focally disrupted and even ruptured basement membrane.

However, in the skin areas that were treated with the agent of the invention, a clearly thickened, continuous and intact basement membrane was observed.

These results show and establish that the topical application of the agent of the present invention results in a remodeling of the discontinuous, damaged basement membrane of the aging skin and a resultant reconstitution of the normal dermo-epidermal interactions.

COSMETIC FORMULATIONS

The term "cosmetic" or "cosmetic composition" as used herein is intended to include all types of products which are applied in any manner directly to the person and is intended to include, in addition to the cosmetic agent invention disclosed herein, conventional ingredients such as lanolin, beeswax, oleic acid, spermaceti, almond oil, castor oil, tracacanth gum, clay, magnesia, talc, metal stearates, chalk, magnesium carbonate, zinc stearate, kaolin, etc.

Said compositions may take the form of fatty or non fatty creams, milky suspensions or emulsions of the water-in-oil or oil-in-water types, lotions, gels or jellies, colloidal or non colloidal aqueous or oily solutions, pastes, soaps, aerosols, soluble tablets (to be dissolved in a fluid, such as water) or sticks.

The amount of active ingredient contained in cosmetic compositions according to the invention applied to the skin may vary between wide limits, depending from the formulation and the frequency of use of said compositions. Generally, said compositions contain from 0.1%-99% by weight of the extracellular connective tissue matrix extract.

The cosmetic compositions used in the method according to the invention may also contain conventional vehicles or carriers, such as solvents, fats, oils and mineral waxes, fatty acids and derivatives thereof, alcohols and derivatives thereof, glycols and derivatives thereof, glycerol and derivatives thereof, sorbitol and derivatives thereof, surface-active agents of the anionic, cationic or nonionic type, emulsifying agents, preserving agents, perfumes, etc.

A few examples of cosmetic compositions used in methods according to this invention are given hereafter. These examples are only illustrative and must not be considered as limiting the scope of the invention. In said examples, the percentages are by weight. In addition, the cosmetic composition according to the present invention can be produced and used in the same manner as in the conventional cosmetics.

The following formulations are exemplary embodiments of the invention, but are not intended to limit the scope of this invention or restrict it to these particular formulations:

CREAM

A cream (oil-in-water) containing the active composition (extracellular connective tissue matrix extract prepared according to the present invention) comprising:
a) glycerol monostearate: 12.0%
cetyl stearyl alcohol ethylene oxide adduct containing about 12 mole ethylene oxide: 1.5%
cetyl stearyl alcohol ethylene oxide adduct containing about 20 mole ethylene oxide: 1.5%
cetyl alcohol: 2.0%
2-octyl-dodecanol: 10.0%
isoctyl stearate: 8.0%
caprylic/capric acid triglyceride: 3.0%
methylparaben: 0.17%
propylparaben: 0.03%
and
b) water, distilled: 46.8%
glycerol: 5.0%
and
c) active composition according to the present invention (prepared as explained above): 10.0%

Mixture a) is heated to approximately 70° C. and mixture b) is likewise heated to approximately 70° C. and then added while stirring to mixture a).

Stirring is continued until the cream has cooled down to approximately 30° C. Then composition c) is added while stirring and the cream is homogenized.

By the term cream used herein are meant all cosmetic materials which include, for instance, hand creams, cleansing creams, milky lotions, cold creams, vanishing creams, hair creams, foundation creams, beauty washes, facial packs and the like.

EMULSION

Oil-in-water emulsion (o/w) containing the active composition (the extracellular connective tissue matrix extract prepared according to the present invention) comprising
a) glycerol monostearate: 3.0%
cetyl stearyl alcohol: 2.0%
cetyl stearyl alcohol ethylene oxide adduct containing about 12 mole ethylene oxide: 1.5%
cetyl stearyl alcohol ethylene oxide adduct containing about 20 mole ethylene oxide: 1.5%
glycerol monooleate: 0.5%
2-octyl-dodecanol: 10.0%
methylparaben: 0.17%
propylparaben: 0.03%
and
b) water, distilled: 66.3%
glycerol: 5 0%
and
c) active composition according to the present invention (as in example 1): 10.0%

Mixture a) is heated to approximately 70° C. and mixture b) is likewise heated to approximately 70° C. and added while stirring to mixture a).

Stirring is continued until the o/w emulsion has cooled down to approximately 30° C. Then composition c) is added while stirring and the o/w emulsion is homogenized.

GEL

A gel containing the active composition (extracellular connective tissue matrix extract prepared according to the present invention) comprising:
a) water, distilled: 65.10%
polyacrylic acid (type Carbopol 940): 0.80%
methylparaben: 0.17%
propylparaben: 0.03% and
b) polyoxethylene (20) sorbitan trioleate: 0.30%
sorbitan monooleate: 0.15%
caprylic/capric acid triglyceride: 2.50% and
c) water, distilled: 20.15%
triethanolamine: 0.80% and
d) active composition according to the present invention (as in example 1): 10.0%

Preparation of the gel is carried out as follows:

For obtaining a), polyacrylic acid is dispersed under rapid stirring in water; then the components of b) are mixed and added under stirring to a); likewise the aqueous triethanolamine solution c) is added under stirring; finally composition d) is added under stirring.

I claim:
1. A cosmetic composition comprising:
(a) an extracellular connective tissue matrix composition comprising collagens, proteoglycans, glycosaminoglycans and non-collagen glycoproteins wherein said collagens, said proteoglycans, said glycosaminoglycans and said non-collagen glycoproteins have each been extracted from an extracellular connective tissue matrix in solubilized form and are in their native structural form, and
(b) a cosmetic carrier.

2. The cosmetic composition of claim 1 wherein the cosmetic carrier is a cream.

3. The cosmetic composition of claim 1 wherein the cosmetic carrier is an oil-in-water emulsion.

4. The cosmetic composition of claim 1 wherein the cosmetic carrier is a lotion.

5. The cosmetic composition of claim 1 wherein the cosmetic carrier is a gel.

6. The cosmetic composition of claim 1 wherein the extracellular connective tissue matrix composition comprises at least about 0.1% of said cosmetic composition.

7. The cosmetic composition of claim 1 wherein said collagens, said proteoglycans, said glycosaminoglycans and said non-collagen glycoproteins are in their in-vivo physiological proportions.

8. The cosmetic composition of claim 1 wherein the collagens comprise collagen types I, III, IV, V, VI and VII.

9. The cosmetic composition of claim 8 wherein said collagens are in their in-vivo physiological proportions.

10. The composition of claim 1 wherein the extracellular connective tissue matrix composition is derived from a mammal.

11. The cosmetic composition of claim 1 wherein the extracellular connective tissue matrix composition is derived from an animal selected from the group consisting of bovine, ovine and porcine.

12. The cosmetic composition of claim 10 or 11 wherein the extracellular connective tissue matrix composition is derived from the tissue selected from the group consisting of placenta tissue, fetal membranes, blood vessels and umbilical cords.

13. An extracellular connective tissue matrix composition comprising collagens, proteoglycans, glycosaminoglycans, and non-collagen glycoproteins wherein said collagens, said proteoglycans, said glycosaminoglycans and said non-collagen glycoproteins have each been extracted from an extracellular connective tissue matrix is solubilized from and are in their native structural form.

14. The extracellular connective tissue matrix composition of claim 13 wherein the extracellular connective tissue matrix is derived from an animal selected from the group consisting of ovine, bovine and porcine.

15. The extracellular connective tissue matrix composition of claim 13 wherein the collagens comprise collagen types I, III, IV, V, VI and VII.

16. The extracellular connective tissue matrix composition of claim 13 wherein said collagens, said proteoglycans, said glycosaminoglycans and said non-collagen glycoproteins are in their in-vivo physiological proportions.

17. The extracellular connective tissue matrix composition of claim 13 wherein the extracellular connective tissue matrix is derived from a mammal.

18. The extracellular connective tissue matrix composition of claim 17 wherein the extracellular connective tissue matrix is derived from the tissue selected from the group consisting of placenta tissue, fetal membranes, blood vessels and umbilical cords.

* * * * *